United States Patent [19]

Wajaroff et al.

[11] Patent Number: 4,781,724
[45] Date of Patent: Nov. 1, 1988

[54] PROCESS FOR THE SIMULTANEOUS DYEING AND PERMANENT SHAPING OF HAIR

[75] Inventors: Theodor Wajaroff; Peter Hartmann, both of Darmstadt, Fed. Rep. of Germany; Kohei Kubo, Tokyo, Japan

[73] Assignee: Wella Aktiengesellschaft, Darmstadt, Fed. Rep. of Germany

[21] Appl. No.: 93,748

[22] PCT Filed: Nov. 26, 1986

[86] PCT No.: PCT/EP86/00682
§ 371 Date: Jul. 22, 1987
§ 102(e) Date: Jul. 22, 1987

[87] PCT Pub. No.: WO87/03474
PCT Pub. Date: Jun. 18, 1987

[30] Foreign Application Priority Data

Dec. 9, 1985 [DE] Fed. Rep. of Germany ....... 3543453

[51] Int. Cl.$^4$ ................................................. A61K 7/13
[52] U.S. Cl. ........................................... 8/426; 8/432; 132/7; 424/72
[58] Field of Search ...................... 8/426, 432; 424/72; 132/7

[56] References Cited

U.S. PATENT DOCUMENTS 3,399,682 9/1968 Isaji ........................................ 8/432

Primary Examiner—Robert A. Wax
Attorney, Agent, or Firm—Michael J. Striker

[57] ABSTRACT

Process for the simultaneous dyeing and permanent shaping of white and gray hair, in which the hair is first treated with a shaping composition, then rinsed with water and treated with a fixing composition, characterized in that a shaping composition is used which comprises a content of at least one red-violet dyeing xanthene dyestuff and a fixing composition with a content of at least one blue dyeing anthraquinone dyestuff. The process, according to the invention, offers the advantage that the unwanted yellow shade in white and gray hair is permanently removed during the hair shaping treatment without an additional dyeing treatment.

11 Claims, No Drawings

PROCESS FOR THE SIMULTANEOUS DYEING AND PERMANENT SHAPING OF HAIR

DESCRIPTION

The invention relates to a process for the permanent shaping of white and gray hair which also involves a simultaneous dyeing of the hair.

In the present conventional process, the permanent shaping of hair is effected in two steps. First, the disulfide bridges of the hair keratin are broken by means of the action of a suitable reducing agent. The hair is then put into its new shape and fixed in the new shape by means of treatment with a suitable oxidizing agent accompanied by the reconnection of the broken disulfide bonds.

The composition used for implementing the first reducing process step contains sulfite, bisulfite or certain mercapto compounds, particularly thioglycolic acid and thiolactic acid, also in the form of their ester or alkaline or ammonium salts, as a hair keratin reducing substance which effects shaping.

These compositions are made either acidic (sulfite, bisulfite and mercaptocarboxylic acid ester) or alkali (alkali and ammonium salts of mercaptocarboxylic acids). In the case of alkaline adjusted shaping compositions the required alkalinity is primarily achieved by means of adding ammonia, organic amines, ammonium- or alkali carbonate and ammonium- or alkali hydrocarbonate.

The permanent shaping of human hair is generally carried out in that the washed and towel dried hair is first divided into a plurality of parts and these parts are then wound on curlers. After the curling process, the curlers are thoroughly moistened with the required quantity of permanent shaping composition. The curlers which are used for a permanent wave have a diameter of approximately 5 to 13 millimeters, whereas curlers having a diameter of more than 13 millimeters are required for hair straightening. In hair straightening, one can also dispense with the use of curlers if the hair is stretched by means of combing during the period in which the keratin reducing composition is allowed to act.

The time during which the shaping composition acts on the hair amounts to approximately 5 to 30 minutes in permanent waving as well as permanent straightening, depending on the constitution of the hair and the degree of reshaping which is desired. This period of action can be reduced by means of applying heat, for example, with the use of a heat radiator or a dryer.

After the required period of action of the shaping composition has elapsed, the hair is rinsed with water and treated with a fixing composition, for example, an aqueous solution of hydrogen peroxide or potassium bromate. The period of action of the fixing composition is usually approximately 10 to 15 minutes. Next, the curlers are removed, the hair is treated a second time for some minutes with the fixing composition, if necessary, and is then thoroughly rinsed with water, styled and dried.

Frequently, however, particularly with white or gray hair, a dyeing or tinting is also desired in addition to a shaping of the hair. It is then necessary to carry out a separate dyeing treatment before or after the shaping treatment. This leads to an excessive strain on the hair, since every dyeing or hair shaping constitutes a serious operation on the hair structure.

A reduction of this stressing of the hair can be achieved by means of a simultaneous hair shaping and hair dyeing treatment. Such a combination of the two treatments also saves time.

For this reason, it has already been attempted repeatedly to carry out the shaping and dyeing of hair in one operation. Thus, a process is known from DE-AS Nos. 1 129 261 and GB-PS 876 663, for example, which enables a simultaneous permanent waving and dyeing of hair, including white and gray hair. This process is based on a shaping composition which consists of an aqueous solution of a keratin reducing active ingredient and a suitable basic dyestuff. The dyestuffs used, such as crystal violet, methylene blue, Fuchsin or malachite green, are in the form of the more stable leuco compounds and are only converted into the actual dyestuff during the subsequent oxidative fixing. In addition, it is suggested in the German Patent Application No. A 16 016, as well as in GB-PS No. 721 831, to add determined acidic water-soluble azo dyestuffs, such as Resorcin Brown, Orange I and Tartrazine, to the hair shaping compositions in order to achieve a tinting of the hair simultaneously with the shaping treatment. For the same purpose, nitro compounds of the general formula $(NO_2)_x RX_y(NHR')_z$ are recommended in FR-PS 1 129 112, wherein R is an aromatic group, X is an amino or hydroxy group, and R' is an aliphatic radical with at least one hydroxy group. Finally, reference is made to the survey article "Dauerwellen and Haarfarben in einem Arbeitsgang" (Permanent Wave and Hair Dyeing in One Operation) by R. Heilingöotter, Kosmetic-Parfüm-Drogen Rundschau 3/4 (1965), pages 35 and 36, in which the possibility of a simultaneous tinting and shaping of the hair by means of the addition of oxidative dyestuffs (in the form of their primary steps) to an alkaline thioglycolate solution is discussed.

However, all previously described processes for the permanent shaping and simultaneous dyeing or tinting of hair have disadvantages, so that the results which are achieved are not always satisfactory. Thus, some of the dyestuffs used, such as certain oxidative hair dyestuffs or the nitro dyestuffs described in FR-PS No. 1 129 112, are unstable compared to the alkaline thioglycolate solution which acts in a strongly reducing manner. They are affected in a reductive manner when stored for longer periods of time and their dyeing power decreases, so that it is not possible to produce preparations which are ready for use. Moreover, the nitro dyes used in FR-PS 1 129 112 have the disadvantage that they comprise only yellow, orange and red dyeing shades. The blue and violet shades which are particularly required for white and gray hair are not obtainable with these nitro dyestuffs, Other dyestuffs which are used for simultaneous hair dyeing during the shaping treatment, such as the dyestuffs described in DE-AS No. 1 129 261 and GB-PS No. 876 663, have only a moderate light fastness.

Therefore, it is the object of the invention to provide a process which makes it possible to dye gray or white hair simultaneously during the shaping treatment better than was previously possible and, accordingly, to eliminate the unwanted yellow shade of the hair.

Surprisingly, it has now been found that the disturbing yellow shade in white or gray hair is eliminated in a particularly advantageous manner during the shaping treatment if certain red violet dyestuffs are added to the shaping composition and certain blue dyestuffs are added to the fixing composition.

Therefore, the subject matter of the invention is a process for the simultaneous dyeing and permanent shaping of white and gray hair in which the hair is first treated with a shaping composition, then rinsed with water, and then treated with a fixing composition, which is characterized in that a shaping composition with a content of at least one red-violet dyeing xanthene dyestuff and a fixing composition with a content of at least one blue dyeing anthraquinone dyestuff are used.

In the process, according to the invention, white or gray hair is washed, rubbed with a towel, possibly moistened preliminarily with a portion of the hair shaping composition, divided into individual strands and wound on curlers. The diameter of the curlers is either approximately 5 to 13 millimeters or approximately 15 to 35 millimeters according to whether a permanent wave or a hair straightening is desired. A quantity of the shaping compositon sufficient for shaping the hair, generally approximately 80 g, is then applied to the wound up hair.

The shaping compositions which are usable in the process described here are those based on conventional hair keratin reducing materials, such as salts of sulfuric acid or certain mercapto compounds, for example, particularly salts or esters of mercaptocarboxylic acids. These shaping compositions contain the reducing compounds in the usual quantities for hair shaping, for example, the ammonium salts of the thioglycolic or thiolactic acids in a concentration of approximately 2 to 12 percent by weight. The pH value of the alkaline shaping composition is generally 7 to 10, wherein the adjustment is preferably effected with ammonia, monoethanolamine, ammonium carbonate or ammonium hydrogen carbonate. In shaping compositions which are made acidic (for example, to pH=6.5 to 6.9), it is preferable to use esters of mercaptocarboxylic acids, such as monothioglycolic acid glycolester or -glycerine ester in a concentration of 2 to 14 percent by weight, as wall as salts of sulfuric acid, for example, sodium-, ammonium- or monoethanol ammonium sulfite, in a concentration of 3 to 8 percent by weight (calculated as $SO_2$).

In order to augment the effect, swelling and penetrating materials, such as urea, melamine, alkali- or ammonium thiocyanate, isopropanol, imidazolidin-2-one, 2-pyrrolidone and 1-methyl-2-pyrrolidone are added to these shaping compositions in a concentration of approximately 0.5 to 50 percent by weight, preferably 2 to 30 percent by weight.

In addition, the shaping compositions used in the process according to the invention contain at least one red-violet dyeing xanthene dyestuff in a concentration of 0.00002 to 0.012 percent by weight, preferably 0.00001 to 0.005 percent by weight.

This xanthene dyestuff is selected from dyestuffs listed in the Colour Index, volume 4, third edition, The Society of Dyers and Colourists, Bradford and London 1971, pages 4417 ff., with the following color index numbers: C.I. 45 410 (D & C Red, Nos. 27 and 28, Acid Red 218, C.I. Solvent Red 48, C.I. Acid Red 92, C. I. Pigment Red 174), C.I. 45 190 (Ext. D & C Red No. 3, Red 401, C.I. Acid Violet 9, C.I. Solvent Violet 10) and C.I. 45 170 (D & C Red Nos. 19 and 37, C-ext. Rot 27, C.I. Basic Violet 10, C.I. Solvent Red 49, C.I. Pigment Red 173, C.I. Pigment Violet 1, Red 213, Red 215).

After allowing it to act for a period sufficient for the permanent shaping of the hair, which amounts to approximately 5 to 30 minutes according to the constitution of the hair, the pH value and the shaping effectiveness of the shaping composition, and depending on the application temperature, the shaping composition is rinsed out with water and the hair is fixed oxidatively. The fixing composition is used in a quantity of approximately 80 to 100 g, according to the fullness of the hair.

Any desired oxidizing agent previously used in fixing compositions can be used for fixing. Examples of such oxidizing agents are potassium bromate, sodium bromate, sodium perborate, hydrogen peroxide and urea peroxide. The concentration of oxidizing agent varies as a function of the application time (5 to 15 minutes, as a rule) and the application temperature. Normally, the oxidizing agents are used in the aqueous fixing compositions in a concentration of approximately 0.5 to 10.0 percent by weight. Of course, the fixing compositions can contain other materials such as weak acids or peroxide stabilizers.

In addition, these fixing compositions contain at least one of the anthraquinone dyestuffs described in the Colour Index, volume 4, third edition, The Society of Dyers and Colourists, Bradford and London 1971, pages 4511 ff., under the following color index numbers: C.I. 69 825 (D & C Blue No. 9, Blue 204, C.I. Vat Blue 6, C.I. Pigment Blue 64), C.I. 60 725 (D & C Violet No. 2, Violet 201, C.I. Solvent Violet 13) and C.I. 60 730 (Ext. D & C Violet No. 2, Violet 401, C.I. Acid Violet 43).

The content of these anthraquinone dyestuffs in the fixing compositions amounts to 0.00002 to 0.012 percent by weight, preferably 0.00001 to 0.01 percent by weight.

Both the shaping composition used in the process according to the invention and the fixing composition can be in the form of an aqueous solution or an emulsion, as well as in concentrated form on an aqueous base, particularly as cream, gel or paste. It is also possible to fill aerosol cans with these compositions under pressure and to dispense them as aerosol foam.

Of course, both the fixing composition and the shaping composition can contain all the usual and known ingredients for such compositions, for example, thickeners such as kaolin, bentonite, fatty acids, higher fatty alcohols, starch, polyacrylic acid, cellulose derivatives, alginates, petrolatum or paraffin oil for example wetting agents or emulsifying agents from the classes of anionic, cationic, amphoteric or non-ionogenic surface-active substances, for example, fatty alcohol sulfates, fatty alcohol ether sulfates, alkyl sulfonates, alkyl benzene sulfates, quaternary ammonium salts, alkyl betaines, oxyethylated fatty alcohols, oxyethylated alkyl phenols, fatty acid alkanolamides or oxyethylated fatty acid esters; also clouding agents, for example, polyethylene glycol ester, or alcohols such as ethanol, propanol, isopropanol or glycerin, for example; dissolving intermediaries, stabilizers, buffer substances, perfume oils, hair conditioning agents, and hair care components such as lanolin derivatives, cholesterin, pantothenic acid or betain, for example. In addition, optical brighteners in the form of derivatives if cumarin, stilbene, naphthalimide, benzoxazol or styryl can be added to these compositions. The aforementioned components are used in quantities which are conventional for such purposes, for example, the wetting agents and emulsifying agents can be contained in these compositions in concentrations of approximately 0.2 to 30 percent by weight, while the thickeners can be contained in a quantity of approximately 0.1 to 25 percent by weight.

Next, the curlers are removed, the fixing composition is rinsed out of the hair with water, and the hair is treated further in the usual manner. As a rule, the hair is set in a water wave subsequent to the permanent shaping. In the case of hair straightening, the fixing composition can also be rinsed off, when the hair is in curlers, and the hair can be dried directly on the curler without unwinding. It is also possible to blow dry the straightened hair directly after removing the curlers and rinsing off the fixing composition.

The hair which is permanently shaped in this manner has an attractive, clear, lustrous white color which is free of yellow shades.

The process, according to the invention, provides the advantage of achieving a shaping of the hair and an elimination of the unwanted yellow shade, which often occurs in white and gray hair, in one operation. By means of this, a treatment of the hair is made possible which is gentle and time-saving simultaneously.

A further advantage of the present invention is the simple differentiation of the shaping composition and the fixing composition by means of the different colors of these two compositions (fixing composition=blue; shaping composition=red violet), by means of which the implementation of the process is safely ensured.

The following examples serve to explain the invention in more detail without restricting it to these examples.

EXAMPLES

Example 1

1 Process for Permanent Wave and Simultaneous Dyeing of White and Gray Hair

White hair, which is up to 50 percent gray, is washed with a mild shampoo. Next, the towel dried hair is wound on curlers having a diameter of 7 to 10 millimeters and is thoroughly moistened repeatedly with a permanent wave liquid of the following composition

| | |
|---|---|
| 23.700 g | ammonium thioglycolate, 50 percent aqueous solution |
| 3.000 g | ammonium carbonate |
| 5.000 g | ammonium hydrogen carbonate |
| 2.000 g | isooctylphenol, oxyethylated with 10 moles ethylene oxide |
| 0.200 g | perfume oil |
| 0.001 g | C.I. Acid Violet 9 (C.I. 45 190) |
| 66.099 g | water |
| 100.000 g | |

The pH value of the permanent wave liquid used is 8.8.

After allowing it to act for a period of 15 minutes, the wound hair is thoroughly rinsed with warm water and then treated with a fixing composition of the following composition, which has a pH value of 6.8:

| | |
|---|---|
| 9.200 g | sodium bromate |
| 1.000 g | 1-carboxymethyl-2-heptadecyl-1-(2-hydroxyethyl)-2-imidazoliniumchloride (Miranol ® DM) |
| 1.000 g | isooctylphenol, oxyethylated with 10 moles ethylene oxide |
| 0.100 g | perfume oil |
| 0.002 g | C.I. Vat Blue 6 (C.I. 69 825) |
| 88.698 g | water |
| 100.000 g | |

After allowing it to act for a period of 5 minutes, the wound hair is rinsed with water and the curlers are removed from the hair. The hair is then set in a water wave and dried under a dryer.

As a result of this treatment, permanently waved hair is obtained, whose white portion has a shining white color free of yellow shades. This coloring is very stable and also withstands repeated hair washing.

Example 2

Process for the Permanent Shaping and Simultaneous Dyeing of White and Gray Hair White hair, which is up to 75 percent gray and which has a clear yellow luster, is washed and rubbed with a towel. Next, the hair is preliminarily moistened with half of a shaping composition which has the following composition

| | |
|---|---|
| 17.3000 g | ammonium sulfite, 34 percent aqueous solution |
| 13.5000 g | sulfuric acid (aqueous solution with 5 percent by weight $SO_2$ content.) |
| 7.5000 g | imidazolidin-2-one |
| 3.5000 g | isopropanol |
| 0.5000 g | octylphenol, oxyethylated with 20 moles ethylene oxide |
| 0.2000 g | perfume oil |
| 0.0002 g | C.I. Acid Red 92 (C.I. 45 410) |
| 57.4998 g | water |
| 100.0000 g | | and a pH value of 6.7 and wound on curlers (diameter of 5 to 7 millimeters for a permanent wave and 15 to 35 millimeters for hair straightening). The rest of the shaping liquid is then distributed on the wound up hair. After letting it act for ten minutes, accompanied by additional heat action, the shaping result is monitored and the shaping treatment is possibly lengthened by 5 minutes.

The hair is then thoroughly rinsed with warm water and then treated with a fixing composition of the following composition:

| | |
|---|---|
| 4.000 g | hydrogen peroxide, 50 percent aqueous solution |
| 1.000 g | sodium lauryl sulfate |
| 0.600 g | orthophosphoric acid, 85 percent aqueous solution |
| 0.200 g | ethylenediaminetetraacetic acid |
| 0.200 g | perfume oil |
| 0.050 g | hippuric acid |
| 0.004 g | C.I. Solvent Violet 13 (C.I. 60 725) |
| 93.946 g | water |
| 100.000 g | |

The pH value of the fixing composition is 2.3.

One proceeds further as in example 1 and obtains an excellently shaped hair whose white portion has a pure white coloring which is free of yellow shades.

Example 3

Process for the Permanent Shaping and Simultaneous Dyeing of White Hair

White, smooth hair is washed and rubbed in a conventional manner. The hair is wound on curlers (diameter 5 to 10 millimeters) and is then thoroughly moistened with a permanent wave composition consisting of a mixture of the

| A. | 5.0000 g | urea |
| | 0.5000 g | cetylstearyl alcohol |
| | 0.6000 g | stearyl alcohol, oxyethylated with 10 moles ethylene oxide |
| | 0.1000 g | sodium lauryl sulfate |
| | 0.5000 g | ammonium dihydrogen phosphate |
| | 2.0000 g | glycerine diacetate |
| | 0.3000 g | perfume oil |
| | 0.0001 g | C.I. Basic Violet 10 (C.I. 45 170) |
| | 90.9999 g | water |
| | 100.0000 g | |
| B. | 16.0000 g | Monothioglycolic acid glycerine ester | two components A and B.

The pH value of the ready-to-use mixture of A and B is 5.3.

The wound up hair is covered with a plastic hood and heated for 15 minutes with a heat radiator.

Next, the hair is rinsed with warm water and treated with a fixing composition of pH 2.6 with the following composition

| 5.0000 g | hydrogen peroxide, 50 percent aqueous solution |
| 0.5000 g | octylphenol, oxyethylated with 20 moles ethylene oxide |
| 0.2000 g | orthophosphoric acid, 85 percent aqueous solution |
| 0.0500 g | acetanilide |
| 0.2000 g | perfume oil |
| 0.0002 g | C.I. Acid Violet 43 (C.I. 60 730) |
| 94.0498 g | water |
| 100.0000 g | | by simultaneously applying 60 g of the fixing composition to the wound up hair, removing the curlers after 7 minutes and re-treating the unwound hair with the remaining 40 g of fixing composition for 3 minutes. The hair is then rinsed with water, set in a water wave and dried.

The permanently waved hair which is obtained in this way has a stable, clear, lustrous white color.

Example 4

Process for Straightening and Simultaneously Dyeing White and Gray Hair

An alkaline (pH=9.6) hair straightening cream of the following composition

| 18.7000 g | ammonium thiolactate, 50 percent aqueous solution |
| 4.2000 g | ammonia, 25 percent aqueous solution |
| 3.0000 g | stearyl alcohol |
| 3.2000 g | stearyl alcohol, oxyethylated with 20 moles ethylene oxide |
| 1.6000 g | petrolatum |
| 0.4000 g | perfume oil |
| 2.0000 g | urea |
| 0.0003 g | C.I. Acid Violet 9 (C.I. 45 190) |
| 0.0002 g | C.I. Acid Red 92 (C.I. 45 410) |
| 66.8995 g | water |
| 100.0000 g | | is uniformly applied to white (10 percent gray portion), very curly hair one part at a time. The hair is repeatedly combed smooth while the straightening composition is allowed to act (10 to 15 minutes).

Next, the hair is rinsed with warm water and fixed oxidatively immediately before using with a solution of

| 9.79 g | sodium bromate |
| 0.20 g | sodium lauryl sulfate |
| 0.01 g | C.I. Solvent Violet 13 (C.I. 60 725) |
| 10.00 g | | in 90 milliliters warm water. The pH value of this fixing composition is 6.9.

After allowing it to act for 10 minutes, the hair is rinsed with water and then blown dry.

The hair is made smooth in this manner and the yellow shade is permanently removed simultaneously.

All percentages given in the present application are percent by weight.

We claim:

1. In a process for permanently shaping and dyeing white or gray hair, in which the hair is washed, towel-dried, wound on curlers, treated with a shaping composition, rinsed, treated with a fixing composition, rinsed, and the curlers removed, the improvement which comprises including in the shaping composition 0.00001 to 0.005% by weight of at least one red-violet dyeing xanthene dyestuff, and in the fixing composition 0.0001 to 0.01% by weight of at least one blue dyeing anthraquinone dyestuff, thereby eliminating any unwanted yellow shade of the hair.

2. The improvement defined in claim 1 wherein the red-violet xanthene dyestuff is selected from the group consisting of the compounds corresponding to Color Index Number C.I. 45 170, C.I. 45 190 or C.I. 45 410.

3. The improvement defined in claim 1 wherein the blue anthraquinone dyestuff is selected from the group consisting of the compounds corresponding to Color Index Number C.I. 60 725, C. I. 60 730, or C.I. 69 825.

4. A process for the permanent shaping and dyeing of gray or white hair whereby unwanted yellow shades of the hair are avoided which comprises the steps of:
   (a) washing the hair;
   (b) towel-drying the hair;
   (c) winding the hair on curlers;
   (d) shaping the hair by applying thereto an effective amount of an aqueous solution of a hair shaping composition which comprises a hair keratin reducing material and 0.0001% to 0.005% by weight of at least one red-violet dyeing xanthene dyestuff, and allowing the shaping composition to act for a period sufficient for the permanent shaping of the hair;
   (e) rinsing the shaping composition out of the hair with water;
   (f) fixing the hair shaped according to step (d) by applying thereto a fixing composition which comprises an effective amount of an oxidative fixing agent and 0.0001% to 0.01% by weight of at least one blue dyeing anthraquinone dyestuff; and
   (g) rinsing the fixing composition out of the hair treated according to step (f) with water, and removing the curlers.

5. The process defined in claim 4 wherein according to step (d) the shaping composition comprises a salt of sulfuric acid or a salt or ester of a mercapto carboxylic acid as the hair keratin reducing material.

6. The process defined in claim 4 wherein according to step (d) the hair keratin reducing material is used in the shaping in a quantity of 2 to 14% by weight.

7. The process defined in claim 4 wherein according to step (d) at least one swelling or penetrating agent is added to the shaping composition.

8. The process defined in claim 7 wherein the swelling or penetrating agent is selected from the group consisting of urea, melamine, alkali or ammonium thiocyanate, isopropanol, imidazolidin-2-one, 2-pyrrolidone and 1-methyl-2-pyrrolidone.

9. The process defined in claim 4, wherein according to step (f) the oxidative fixing agent is selected from the group consisting of hydrogen peroxide, sodium bromate, potassium bromate, sodium perborate, and urea peroxide.

10. The process defined in claim 4 wherein the red-violet dyeing xanthene dyestuff which is included in the shaping composition employed during step (d) is selected from the group consisting of the compounds corresponding to Color Index No. C.I. 45 170, C.I. 45 190 or C.I. 45 410.

11. The process defined in claim 4 wherein the blue dyeing anthraquinone dyestuff which is included in the fixing composition employed during step (f) is selected from the group consisting of the compounds corresponding to Color Index number C.I. 60 725, C. I. 60 730 or C.I. 69 825.

* * * * *